(12) United States Patent
Aizawa et al.

(10) Patent No.: US 8,993,345 B2
(45) Date of Patent: Mar. 31, 2015

(54) METHOD OF PRODUCING FUNCTIONAL MOLECULE-CONTAINING SILICA NANOPARTICLES ON WHICH BIOMOLECULES ARE BONDED

(71) Applicant: Furukawa Electric Co., Ltd., Tokyo (JP)

(72) Inventors: Hideki Aizawa, Tokyo (JP); Michio Ohkubo, Tokyo (JP); Masataka Nishida, Tokyo (JP)

(73) Assignee: Furukawa Electric Co., Ltd., Tokyo (JP)

( * ) Notice: Subject to any disclaimer, the term of this patent is extended or adjusted under 35 U.S.C. 154(b) by 0 days.

(21) Appl. No.: 14/063,666

(22) Filed: Oct. 25, 2013

(65) Prior Publication Data

US 2014/0051186 A1  Feb. 20, 2014

Related U.S. Application Data

(63) Continuation of application No. PCT/JP2012/061055, filed on Apr. 25, 2012.

(30) Foreign Application Priority Data

Apr. 26, 2011  (JP) .................. 2011-097880

(51) Int. Cl.
*G01N 33/532* (2006.01)
*C07K 17/14* (2006.01)
*G01N 33/543* (2006.01)
*G01N 33/552* (2006.01)
*G01N 33/558* (2006.01)

(52) U.S. Cl.
CPC .......... *C07K 17/14* (2013.01); *G01N 33/54346* (2013.01); *G01N 33/54353* (2013.01); *G01N 33/552* (2013.01); *G01N 33/558* (2013.01)
USPC ............... 436/501; 436/86; 436/94; 436/172; 436/518; 436/527; 436/534; 530/391.1

(58) Field of Classification Search
None
See application file for complete search history.

(56) References Cited

U.S. PATENT DOCUMENTS

2003/0124564 A1* 7/2003 Trau et al. .......................... 435/6
2006/0183246 A1* 8/2006 Wiesner et al. ............... 436/524
2008/0220448 A1 9/2008 Blincko et al.
2008/0293584 A1 11/2008 Aizawa et al.
2009/0068639 A1* 3/2009 Aizawa et al. .................... 435/5

FOREIGN PATENT DOCUMENTS

| JP | 2009-222718 A | 10/2009 |
| JP | 2010-14631 A | 1/2010 |
| JP | 2010-509192 A | 3/2010 |
| JP | 2010-100542 A | 5/2010 |
| JP | 2011-27693 A | 2/2011 |
| WO | WO 2007/074722 A1 | 7/2007 |

OTHER PUBLICATIONS

A print-out retrieved from http://www.piercenet.com/product/emcs on Apr. 4, 2014.*
A print-out retrieved from http://www.piercenet.com/method/carbodiimide-crosslinker-chemistry#carbodiimide on Apr. 4, 2014.*
Holtzhauer, "Basic Methods for the Biochemical Lab," Springer, 2006, pp. 129-131.*
Wang et al., "Bioconjugated Nanoparticles for Biotechnology and Analysis," In: "Nanotechnology in Biology and Medicine: Methods, Devices, and Applications," Tuan Vo-Dinh (ed.), CRC Press, 2007, Chapter 19, pp. 19-1, 19-3, 19-4.*
International Search Report Issued in PCT/JP2012/061055, mailed on Aug. 14, 2012.

* cited by examiner

*Primary Examiner* — Galina Yakovleva
(74) *Attorney, Agent, or Firm* — Birch, Stewart, Kolasch & Birch, LLP

(57) ABSTRACT

A method of producing functional molecule-containing silica nanoparticles on which a biomolecule is bonded, containing the steps of:

allowing silica nanoparticles containing a functional molecule and having a thiol group on a surface thereof to coexist with a linker molecule having a maleimido group and a carboxyl group in an aprotic solvent, thereby allowing formation of a thioether bond between the thiol group and the maleimido group, and obtaining functional molecule-containing silica nanoparticles on which the linker molecule is bonded; and allowing the functional molecule-containing silica nanoparticles on which the linker molecule is bonded to coexist with carbodiimide and a biomolecule having an amino group in an aqueous solvent, thereby allowing formation of an amide bond between the carboxyl group active esterified by the carbodiimide, and the amino group of the biomolecule.

10 Claims, 1 Drawing Sheet

METHOD OF PRODUCING FUNCTIONAL MOLECULE-CONTAINING SILICA NANOPARTICLES ON WHICH BIOMOLECULES ARE BONDED

CROSS-REFERENCE TO RELATED APPLICATIONS

This application is a Continuation of PCT International Application No. PCT/JP2012/061055 filed on Apr. 25, 2012, which claims priority under 35 U.S.C 119(a) to Application No. 2011-097880 filed Apr. 26, 2011 in Japan, all which are hereby expressly incorporated by reference in the present application.

TECHNICAL FIELD

The present invention relates to a method of producing functional molecule-containing silica nanoparticles, the surface of which a biomolecule is bonded on.

BACKGROUND ART

Fine particles having a diameter of from several nanometers to about 1 micrometer have been recently applied in various fields and attracted attention. The above-described fine particles include, for example, porous silica particles and zeolite particles to be used for an adsorbent or a catalyst, carbon black, metal oxide particles and inorganic compound particles to be used for a pigment, metal nanoparticles to be used for a conductive material, and silica particles to be used for a reinforcing agent of resin, and thus, material and use of the fine particles are wide-ranging. Moreover, with regard to semiconductor nanoparticles, silica nanoparticles containing a fluorochrome, and so forth, an application as new labeling particles is expected particularly in a field of biotechnology. In addition, silica nanoparticles containing a pigment with high concentration have a high molar extinction coefficient, and thus, an application thereof as further highly sensitive labeling particles is expected.

The above-described labeling particles can be used as a labeling reagent that can be used for detection, quantitative determination, dyeing or the like of a target molecule, by bonding a biomolecule (protein, nucleic acid or the like) having bonding capability with a specific target molecule on the surface of the particles.

SUMMARY OF INVENTION

In the case where silica nanoparticles containing a functional molecule such as a fluorochrome (hereinafter, occasionally referred to as functional molecule-containing silica nanoparticles) are used as labeling particles, as a method for bonding a biomolecule on the surface thereof, a method for allowing bonding by physical adsorption such as hydrophobic interaction and the like; a method for coating the surface of silica nanoparticles with a specific polymer, and then allowing covalent bonding of a functional group of the polymer with a functional group in the biomolecule; and the like are known. In the latter, a method for allowing a cationic polymer and an anionic polymer to bond onto silica nanoparticles by an alternating adsorption process, and bonding the biomolecule through a functional group of the polymer; a method for coating a polysaccharide having a functional group such as a carboxyl group on silica nanoparticles to bond the biomolecule with the functional group of the polysaccharide; and the like are known.

The present inventors focused attention on the fact that, with regard to a labeling reagent in which a biomolecule is physically adsorbed on functional molecule-containing silica nanoparticles, the biomolecule gradually dissociates from the functional molecule-containing silica nanoparticles over time, and as a result, performance as the labeling reagent easily decreases. Further, the present inventors focused attention also on the fact that, with regard to the labeling reagent in which a biomolecule is physically adsorbed on the functional molecule-containing silica nanoparticles, if a solid phase such as a substrate, a membrane and a container each having higher affinity with the biomolecule exists, the biomolecule bonds with these solid phases with higher affinity, and as a result, the biomolecule is peeled off from the functional molecule-containing silica nanoparticles, and the performance as the labeling reagent cannot be effectively developed. In particular, as in the case of an immunochromatography reagent in a form of supporting the labeling reagent onto a carrier such as a pad through a drying step, the biomolecule further strongly bonds with the carrier such as the pad, and conversely, further easily dissociates from the functional molecule-containing silica nanoparticles.

Moreover, the present inventors focused attention also on the fact that, with regard to a labeling reagent prepared by allowing covalent bonding of a functional group of a polymer coated on functional molecule-containing silica nanoparticles with a functional group of a biomolecule, although the biomolecule is hardly peeled off from a surface of the functional molecule-containing silica nanoparticles and can stably exist, strict control of the amount of the polymer to be coated is difficult, and as a result, keeping of constant quality of prepared labeling reagent is difficult. If the constant quality of the labeling reagent is not kept, an inspection result using the labeling reagent will also become poor in reproducibility.

The present invention is contemplated for providing a production method by which the functional molecule-containing silica nanoparticles on which a biomolecule is strongly and stably bonded can be obtained with high reproducibility.

Further, the present invention is contemplated for providing functional molecule-containing silica nanoparticles on which a biomolecule is strongly and stably bonded.

Further, the present invention is contemplated for providing a colloid, formed by dispersing the functional molecule-containing silica nanoparticles on which a biomolecule is bonded into a dispersion medium.

Further, the present invention is contemplated for providing an analytical reagent, containing the functional molecule-containing silica nanoparticles on which a biomolecule is bonded.

The object of the present invention has been achieved by the following means.

<1> A method of producing functional molecule-containing silica nanoparticles on which a biomolecule is bonded, containing the steps of:

allowing silica nanoparticles containing a functional molecule and having a thiol group on the surface thereof to coexist with a linker molecule having a maleimido group and a carboxyl group in an aprotic solvent, thereby allowing formation of a thioether bond between the thiol group and the maleimido group, and obtaining functional molecule-containing silica nanoparticles on which the linker molecule is bonded; and allowing the functional molecule-containing silica nanoparticles on which the linker molecule is bonded to coexist with a carbodiimide and a biomolecule having an amino group in an aqueous solvent, thereby allowing formation of an amide bond between the carboxyl group active esterified by the carbodiimide, and the amino group of the biomolecule.

<2> A method of producing functional molecule-containing silica nanoparticles on which a biomolecule is bonded, containing the steps of:

allowing silica nanoparticles containing a functional molecule and having a thiol group on the surface thereof to coexist with a linker molecule having a maleimido group and a carboxyl group in an aprotic solvent, thereby allowing formation of a thioether bond between the thiol group and the maleimido group, and obtaining functional molecule-containing silica nanoparticles on which the linker molecule is bonded;

allowing the functional molecule-containing silica nanoparticles on which the linker molecule is bonded to coexist with a carbodiimide in an aqueous solvent, thereby allowing active esterification of the carboxyl group; and allowing coexistence of a biomolecule having an amino group in the aqueous solvent, thereby forming an amide bond between the active ester group and the amino group of the biomolecule.

<3> A method of producing functional molecule-containing silica nanoparticles on which a biomolecule is bonded, containing the steps of:

allowing silica nanoparticles containing a functional molecule and having a thiol group on the surface thereof to coexist with a linker molecule having a maleimido group and an active ester group in an aprotic solvent, thereby allowing formation of a thioether bond between the thiol group and the maleimido group, and obtaining functional molecule-containing silica nanoparticles on which the linker molecule is bonded; and allowing the functional molecule-containing silica nanoparticles on which the linker molecule is bonded to coexist with a biomolecule having an amino group in an aqueous solvent, thereby allowing formation of an amide bond between the active ester group and the amino group of the biomolecule.

<4> The production method according to <1> or <2>, wherein the linker molecule is selected from the group consisting of maleimidoacetic acid, 4-maleimidobutyric acid, 5-maleimidovaleric acid, maleimidocaproic acid and 3-maleimidobenzoic acid.

<5> The production method according to <3>, wherein the linker molecule is selected from the group consisting of N-(6-maleimidocaproyloxy)succinimide, 4-(N-maleimidomethyl)cyclohexanecarboxylic acid N-hydroxysuccinimide ester and N-(m-maleimidobenzoyloxy)succinimide.

<6> The production method according to any one of <1> to <5>, containing the following steps for preparing the silica nanoparticles containing the functional molecule and having the thiol group on the surface thereof:

mixing organoalkoxysilane having the functional molecule and tetraalkoxysilane in an ammonia-containing aqueous solvent to allow formation of silica core particles containing the functional molecule in the solvent, thereby obtaining a dispersion liquid of the core particles; and adding organoalkoxysilane having the thiol group and TEOS to the dispersion liquid obtained in the above step, thereby allowing formation of a shell layer on the silica core particles.

<7> The production method according to any one of <1> to <6>, wherein the aprotic solvent is dimethylformamide or dimethylsulfoxide.

<8> The production method according to any one of <1> to <7>, wherein the mean particle diameter of the functional molecule-containing silica nanoparticles on which the biomolecule is bonded is from 20 to 500 nm.

<9> The production method according to any one of <1> to <8>, wherein the biomolecule is selected from the group consisting of a protein, a polyamino acid, a peptide, a nucleic acid, a peptide nucleic acid, a sugar, a sugar chain, a ligand, a receptor and an aptamer.

<10> The production method according to any one of <1> to <8>, wherein the biomolecule is selected from the group consisting of an antibody and an antigen.

<11> The production method according to <10>, wherein the antibody is selected from the group consisting of an immunoglobulin, $F(ab')_2$, Fab, a chemically synthesized polyamino acid, a recombinant protein and a recombinant polyamino acid.

<12> The production method according to any one of <1> to <11>, wherein the functional molecule is selected from the group consisting of a fluorescent molecule, a light-absorbing molecule, a magnetic molecule, a radioactive molecule and a pH-sensitive molecule.

<13> The production method according to any one of <1> to <12>, wherein the bonding amount of the biomolecule is controlled by the amount of the thiol group.

<14> The production method according to <13>, wherein the amount of sulfur element in the silica nanoparticles containing the functional molecule and having the thiol group on the surface thereof is from 100 ppm to 10,000 ppm with respect to the weight of the silica nanoparticles.

<15> Functional molecule-containing silica nanoparticles on which a biomolecule is bonded having a structure in which a thiol group of the functional molecule-containing silica nanoparticles, and a maleimido group of a linker molecule are bonded by a thioether bond; and a structure in which a carboxyl group or active ester group of the linker molecule, and an amino group of the biomolecule are bonded by an amide bond.

<16> The functional molecule-containing silica nanoparticles on which the biomolecule is bonded according to <15>, wherein the linker molecule is selected from the group consisting of maleimidoacetic acid, 4-maleimidobutyric acid, 5-maleimidovaleric acid, maleimidocaproic acid, 3-maleimidobenzoic acid, N-(6-maleimidocaproyloxy)succinimide, 4-(N-maleimidomethyl)cyclohexanecarboxylic acid N-hydroxysuccinimide ester and N-(m-maleimidobenzoyloxy)succinimide.

<17> The functional molecule-containing silica nanoparticles on which the biomolecule is bonded according to <15> or <16>, wherein the mean particle diameter of the functional molecule-containing silica nanoparticles on which a biomolecule is bonded is from 20 to 500 nm.

<18> The functional molecule-containing silica nanoparticles on which the biomolecule is bonded according to any one of <15> to <17>, wherein the biomolecule is selected from the group consisting of a protein, a polyamino acid, a peptide, a nucleic acid, a peptide nucleic acid, a sugar, a sugar chain, a ligand, a receptor and an aptamer.

<19> The functional molecule-containing silica nanoparticles on which the biomolecule is bonded according to <18>, wherein the biomolecule is an antibody or an antigen.

<20> The functional molecule-containing silica nanoparticles on which the biomolecule is bonded according to <19>, wherein the antibody is selected from the group consisting of an immunoglobulin, $F(ab')_2$, Fab, a chemically synthesized polyamino acid, a recombinant protein and a recombinant polyamino acid.

<21> A colloid formed by dispersing the functional molecule-containing silica nanoparticles on which the biomolecule is bonded according to any one of <15> to <20> into a dispersion medium.

<22> The colloid according to <21>, wherein the dispersion medium is a buffer solution.

<23> An analytical reagent containing the functional molecule-containing silica nanoparticles on which the biomolecule is bonded according to any one of <15> to <20>.

According to the method of producing functional molecule-containing silica nanoparticles on which a biomolecule is bonded according to the present invention (hereinafter, occasionally referred to simply as the production method of the present invention), functional molecule-containing silica nanoparticles, the surface of which a biomolecule is strongly bonded on by a covalent bond can be obtained. Moreover, according to the production method of the present invention, a biomolecule in an amount corresponding to the amount of a thiol group on the surface of the functional molecule-containing silica nanoparticles can be bonded. Hence, the bonding amount of the biomolecule can be precisely controlled.

In the functional molecule-containing silica nanoparticles on which a biomolecule is bonded according to the present invention (hereinafter, occasionally referred to as biomolecule-bonding functional silica nanoparticles of the present invention), the biomolecule is strongly and stably bonded with the functional molecule-containing silica nanoparticles by the covalent bond through the linker molecule. Dissociation of the biomolecule from the functional molecule-containing silica nanoparticles is therefore hardly caused. Accordingly, a change of performance over time is less in any of a dry state and a dispersion state. Moreover, use as the labeling reagent allows an analysis excellent in reproducibility and reliability with high sensitivity.

The colloid according to the present invention is formed by dispersion of the biomolecule-bonding functional silica nanoparticles according to the present invention in which a change of performance is small over time, and thus is excellent in preservation stability.

The analytical reagent according to the present invention contains, as the labeling reagent, the biomolecule-bonding functional silica nanoparticles according to the present invention in which a change of performance is small over time, and thus is excellent in reproducibility and reliability of an analytical result.

Other and further features and advantages of the present invention will appear more fully from the following description, appropriately referring to the accompanying drawing.

BRIEF DESCRIPTION OF DRAWINGS

In FIG. 2, (a) shows a top view and (b) shows a longitudinal sectional view.

MODE FOR CARRYING OUT THE INVENTION

Figure 1:
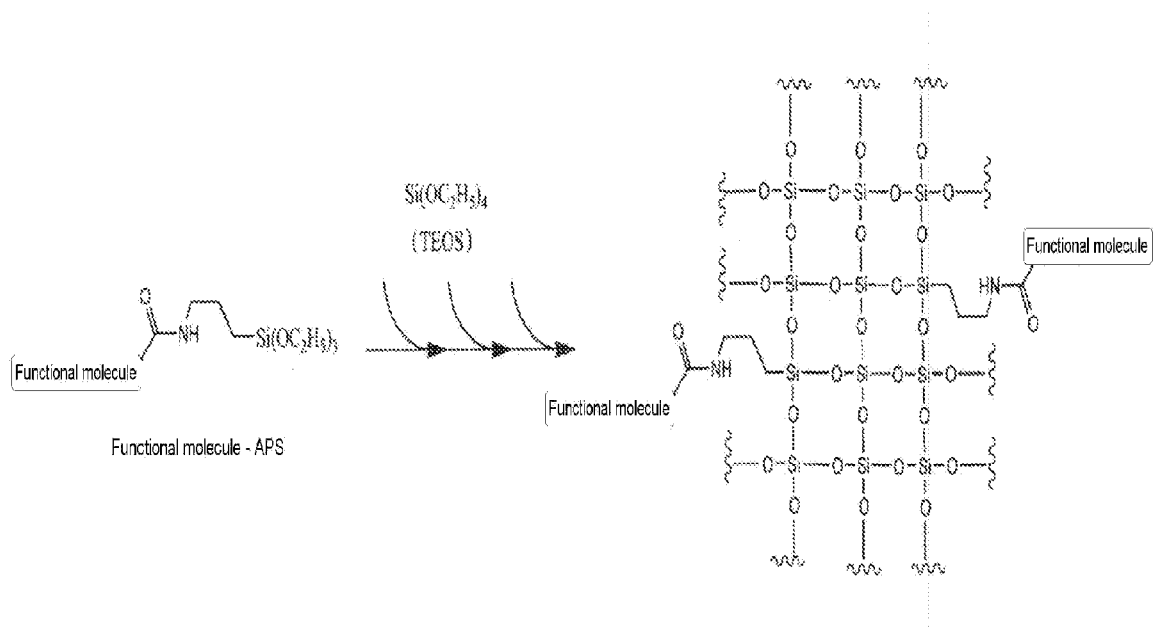
FIG. 1 is a drawing showing a reaction scheme for obtaining functional molecule-containing silica particles using APS as a silane coupling agent, and TEOS as a silane compound.

Hereinafter, the present invention is described in detail based on a preferable embodiment thereof.

In the production method of the present invention, silica nanoparticles containing a functional molecule and having a thiol group on the surface thereof are used. The silica nanoparticles are provided with performance as what is called labeling particles. The production method of the present invention includes a method for allowing covalent bonding of a specific linker molecule with the silica nanoparticles through the thiol group of the silica nanoparticles, and further allowing covalent bonding of a biomolecule to another site of the linker molecule, thereby obtaining functional molecule-containing silica nanoparticles on which the biomolecule is bonded in an amount corresponding to the amount of the thiol group of the silica particles. The thus obtained functional molecule-containing silica nanoparticles on which the biomolecule is bonded can be used, as a labeling reagent, for various kinds of analytical reagents such as a diagnostic reagent and an inspection reagent.

The functional molecule to be incorporated into the above-described functional molecule-containing silica nanoparticles is not particularly limited, and specific examples include a fluorescent molecule, a light-absorbing molecule, a magnetic molecule, a radioactive molecule and a pH-sensitive pigment molecule.

The functional molecule-containing silica nanoparticles can be prepared by allowing the functional molecule to coexist with a silane coupling agent, thereby obtaining a product (organosiloxane component) in which the functional molecule and the silane coupling agent are bonded by a covalent bond, an ionic bond or any other chemical bond, or physical adsorption, and allowing condensation polymerization of this product with one kind or two or more kinds of silane compounds (siloxane component) to form a siloxane bond.

The above-described silane compound (siloxane component) is not particularly limited, and one kind or two or more kinds selected from, for example, tetraethoxysilane (TEOS), γ-mercaptopropyltrimethoxysilane (MPS), γ-mercaptopropyltriethoxysilane, γ-aminopropyltriethoxysilane (APS), 3-thiocyanatopropyltriethoxysilane, 3-glycidyloxypropyltriethoxysilane, 3-isocyanatopropyltriethoxysilane and 3-[2-(2-aminoethylamino)ethylamino]propyltriethoxysilane can be used. Among those, TEOS can be preferably used.

In addition, as the silane compound used for condensation polymerization, one having a thiol group, such as MPS, can also be used. In this case, the thiol group exists on the surface of the functional molecule-containing silica nanoparticles obtained. Thus, in this case, an operation for introducing a thiol group onto the surface of the functional molecule-containing silica nanoparticles as described later is not necessary.

In the case of allowing covalent bonding of a functional molecule with the silane coupling agent, for example, a functional molecule having an active group such as an N-hydroxysuccinimide (NHS) ester group, a maleimido group, an isocyanate group, an isothiocyanate group, an aldehydro group, a p-nitrophenyl group, a diethoxymethyl group, an epoxy group and a cyano group, and a silane coupling agent having a functional group (for example, an amino group, a hydroxyl group or a thiol group) that can react with these active groups can be used.

Specific examples of the functional molecule having a NHS ester group may include NHS ester group-containing fluorescence dye compounds such as 5- (and -6)-carboxytetramethylrhodamine NHS ester (trade name, manufactured by emp Biotech GmbH), DY550-NHS ester represented by the following formula and DY630-NHS ester represented by the following formula (trade name for both, manufactured by Dyomics GmbH).

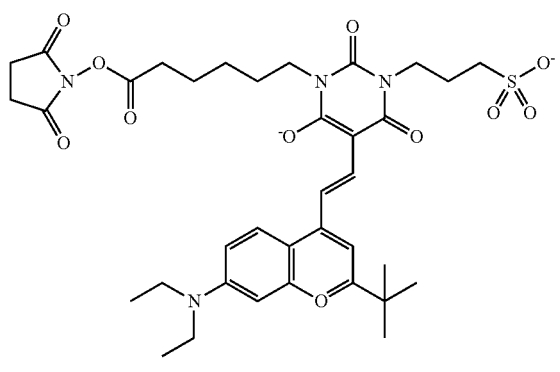

DY550-NHS Ester

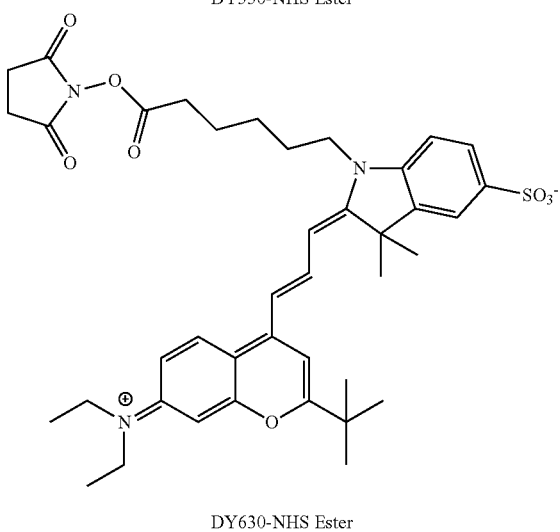

DY630-NHS Ester

When the functional molecule has a succinimide group, the functional molecule can be bonded with a silane coupling agent having an amino group. Examples of the silane coupling agent having the amino group include γ-aminopropyltriethoxysilane (APS), 3-[2-(2-aminoethylamino)ethylamino]propyltriethoxysilane, 3-(2-aminoethylamino) propyldimethoxymethylsilane, 3-aminopropyltrimethoxysilane, and the like. Among them, APS can be preferably used.

A shape of the functional molecule-containing silica nanoparticles prepared as mentioned above is spherical, in which a ratio of major axis length to minor axis length is 2 or less. Further, the mean particle diameter is preferably from 1 to 1000 nm, more preferably from 20 to 500 nm.

Silica nanoparticles having an intended mean particle diameter can be obtained by ultrafiltration by using an ultrafiltration membrane such as YM-10 and YM-100 (trade names for both, manufactured by Millipore Corporation), or by recovering a supernatant or precipitates after performing centrifugal separation with suitable acceleration of gravity.

Subsequently, a method for introducing a thiol group onto the surface of the functional molecule-containing silica nanoparticles is explained.

Introduction of the thiol group onto the surface of the silica nanoparticles can be achieved by an ordinary method. For example, a method described in Journal of Colloid and Interface Science, 159, 150-157 (1993) or WO 2007/074722 A1 can be employed.

For example, functional molecule-containing silica nanoparticles are dispersed into a mixed solvent of water and ethanol, a silane compound having a thiol group (3-mercaptopropyltrimethoxysilane, 3-mercaptopropyltriethoxysilane, or the like) and aqueous ammonia are added thereto, and the resultant mixture is stirred, and thus the thiol group can be introduced onto the surface of the functional molecule-containing silica nanoparticles. The above-described mixed solvent of water and ethanol is preferably adjusted to be 1/10 to 1/1 in a volume ratio of water/ethanol. Moreover, the final concentration of the functional molecule-containing silica nanoparticles is preferably adjusted to be from 0.1 to 2 wt %, and the amount of the silane compound having the thiol group to be added is preferably adjusted to be from 0.2 mmol to 20 mmol with respect to 1 g of the functional molecule-containing silica nanoparticles. Moreover, with regard to addition of aqueous ammonia, 28% aqueous ammonia is preferably added to be from 0.2 to 2 wt % as ammonia concentration.

The above-described method for introducing the thiol group requires time and labor because operations include preparing the functional molecule-containing silica nanoparticles as a core, separating the particles and washing the particles, and then introducing the thiol group thereonto. Moreover, introduction of an intended amount of the thiol group with high reproducibility is also difficult. Ordinarily, in order to introduce the thiol group with high reproducibility, the silane compound having the thiol group is sufficiently allowed to react. However, this sufficient reaction tends to increase the amount of the thiol group to be introduced onto the surface of the functional molecule-containing silica nanoparticles. As a result, hydrophobicity on the surface rises (more specifically, an absolute value of zeta potential decreases), and aggregation of particles with each other is easily caused.

Accordingly, the functional molecule-containing silica nanoparticles having the thiol group are preferably prepared by a simpler method, the simpler method allowing control of the introducing amount of the thiol group in a free manner with high reproducibility.

As such a preparation method, a method including the following steps is examplified:

mixing, in an aqueous ammonia-containing solvent, organoalkoxysilane having a functional molecule and tetraalkoxysilane, thereby allowing formation of silica core particles containing the functional molecule in the solvent, and obtaining a dispersion liquid of these core particles, and adding organoalkoxysilane having a thiol group and TEOS to the dispersion liquid obtained in the above-described step, thereby allowing formation of a shell layer on the silica core particles.

By adjusting a ratio of addition of the above-described organoalkoxysilane having the thiol group and the above-described TEOS, the amount of the thiol group to be introduced can be adjusted in a free manner.

In the method through the above-described steps, an operation can be continuously performed from preparation of the functional molecule-containing silica nanoparticles to introduction of the thiol group, and therefore operation time and labor are significantly improved.

The absolute value of zeta (ζ) potential of the functional molecule-containing silica nanoparticles on which the thiol group is introduced is preferably from 20 to 70 mV. In the particles in which the absolute value of zeta potential is within the above-described range, aggregation is suppressed and dispersibility is further improved.

The zeta potential can be measured using Zetasizer Nano (trade name, manufactured by Malvern Instruments Ltd.), ELS-Z1 (trade name, manufactured by Otsuka Electronics Co., Ltd.), NICOMP 380 ZLS (trade name, manufactured by IBC Advanced Technologies, Inc.) or the like.

The amount of the thiol group on the surface of the functional molecule-containing silica nanoparticles can be evaluated by analyzing the amount of a sulfur element by an elemental analysis. The content of the sulfur element in the functional molecule-containing silica nanoparticles having the thiol group used in the present invention is preferably 100 ppm to 10,000 ppm with respect to the weight of the functional molecule-containing silica nanoparticles having the thiol group. When the content of the sulfur element is 100 ppm or less, the amount of the biomolecule bonded through the linker molecule is small, and adequate functioning as the labeling reagent is hard. Moreover, when the content of the sulfur element is 10,000 ppm or more, an amount of the thiol group present on the surface of the particles is too large, and hydrophobicity on the surface of the silica nanoparticles increases, and thus an increase in nonspecific adsorption by hydrophobic interaction and a decrease in dispersibility of particles are easily caused. The content of the sulfur element in the functional molecule-containing silica nanoparticles having the thiol group used in the present invention is more preferably from 100 ppm to 5,000 ppm, further preferably from 200 ppm to 2,000 ppm with respect to the weight of the functional molecule-containing silica nanoparticles having the thiol group.

The above-described content of the sulfur element can be measured by a combustion method.

Specifically, from 5 to 50 μg of silica nanoparticles is put into a metal capsule such as a Ni capsule, and the amount of sulfur dioxide ($SO_2$) produced by combustion is quantitatively determined, and thus the amount of the sulfur element can be measured.

The linker molecule used in the present invention includes a molecule having a maleimido group, and a carboxyl group or an active ester group in the molecule, and preferably a molecule in which the maleimido group, and the carboxyl group or the active ester group are linked through a saturated hydrocarbon, an unsaturated hydrocarbon and/or an aromatic hydrocarbon.

Specific examples of the linker molecule having the maleimido group and the carboxyl group in the molecule include maleimidoacetic acid, 4-maleimidobutyric acid, 5-maleimidovaleric acid, maleimidocaproic acid, 3-maleimidobenzoic acid, and the like.

Specific examples of the molecule having maleimido group and the active ester group in the molecule include N-(6-maleimidocaproyloxy)succinimide, 4-(N-maleimidomethyl)cyclohexanecarboxylic acid N-hydroxysuccinimide ester, N-(m-maleimidobenzoyloxy)succinimide, and the like.

The molecular weight of the linker molecule is not particularly limited, and preferably from 150 to 5000 Da.

In the production method of the present invention, the thioether bond is first allowed to form between the maleimido group of the above-described linker molecule and the thiol group that is introduced onto the surface of the functional molecule-containing silica nanoparticles, and thus the functional molecule-containing silica nanoparticles on which the linker molecule is bonded is obtained.

A reaction of the above-described maleimido group with the thiol group is performed in an aprotic solvent. The reason is that use of a protic solvent causes a reaction of the maleimido group with a solvent molecule, resulting in a decrease in reactivity with the thiol group. The above-described aprotic solvent is not particularly limited, if the solvent can disperse the silica nanoparticles, and specific examples include N,N-dimethylformamide, dimethyl sulfoxide, and the like.

Ordinarily, in a biochemical field, the reaction of the maleimido group with the thiol group is performed using an aqueous solvent unavoidably in many cases in order to prevent a decrease in activity of the biomolecule or the like. However, in the production method of the present invention, the maleimido group only needs to be reacted with the thiol group of the functional molecule-containing silica nanoparticles, and needs no reaction with the biomolecule, and therefore the reaction of the maleimido group with the thiol group can be significantly efficiently performed in the aprotic solvent.

In the above-described reaction, a concentration of the functional molecule-containing silica nanoparticles having the thiol group in the aprotic solvent is preferably adjusted to be from 0.05 to 2% by mass, and from 0.1 to 5 mg of linker molecule is preferably allowed to react with 1 mg of the functional molecule-containing silica nanoparticles having the thiol group. The reaction temperature is preferably from 0 to 60° C., more preferably from 0 to 40° C. The reaction time is preferably 5 minutes or more, more preferably from 5 to 120 minutes.

When the biomolecule is bonded with the linker part of the functional molecule-containing silica nanoparticles on which the linker molecule is bonded prepared as described above, the functional molecule-containing silica nanoparticles on which the biomolecule is bonded is prepared. The above-described biomolecule is bonded by amide bond with a moiety of the carboxyl group or the active ester group of the linker molecule through the amino group of the biomolecule.

When a linker molecule has a carboxyl group, the carboxyl group is subjected to active esterification by using a carbodiimide, and the amide bond is formed by allowing this active ester group to react with the amino group of the biomolecule. In this case, the reaction may be performed by allowing coexistence of the functional molecule-containing silica nanoparticles on which the linker molecule is bonded, the carbodiimide and the biomolecule having the amino group in the aqueous solvent to simultaneously progress an active esterification reaction of the carboxyl group of the linker molecule, and a bonding reaction of the active ester group and the amino group of the biomolecule, or allowing coexistence of the functional molecule-containing silica nanoparticles on which the linker molecule is bonded and the carbodiimide in the aqueous solvent in advance, then mixing with the biomolecule having the amino group in a state in which the active esterification reaction of the carboxyl group of the linker molecule is progressed in advance, to allow a reaction of the active ester group and the amino group of the biomolecule.

Specific examples of the above-described active ester group include o-acylisourea.

On the other hand, when the linker molecule has an active ester group, this active ester group can be directly bonded by amide bond with the amino group in the biomolecule. This bonding reaction is also performed in the aqueous solvent.

Specific examples of the above-described biomolecule include a protein molecule such as an antigen, an antibody or the like, polyamino acid, a molecule of nucleic acid such as DNA, RNA or the like, peptide nucleic acid, a sugar, a sugar chain, a ligand, a receptor, a peptide, an aptamer and a physiologically active substance, and the like.

Here, the antibody means a protein or a polyamino acid that is bonded with a specific antigen. The antibody includes an immunoglobulin, $F(ab')_2$ and Fab that are obtained by decomposing the immunoglobulin, artificially chemically synthesized polyamino acid, and recombinant protein and recombinant polyamino acid that are prepared using *Escherichia coli*, yeast or the like as an expression system.

Further, the above ligands mean a substance capable of specifically bonding to a specific protein and the like (receptors), and examples thereof include substrates capable of bonding to enzyme, coenzymes, regulatory factors, hormones, neurotransmitters, and the like, and thus, the ligands include low molecular-weight molecules as well as polymer substances.

The physiologically active substances include not only natural organic compounds but also bioactive compounds artificially prepared, environmental hormones, and the like.

In the case where the above-described biomolecule inherently has an amino group, the biomolecule can be used as the biomolecule having the amino group in the present invention. Moreover, even in the case where the above-described biomolecule has no amino group, the amino group is artificially introduced, and thus the resultant product can be used as the biomolecule having the amino group in the present invention.

The above-described aqueous solvent is not particularly limited, but preferably is a buffer solution, and an ordinary aqueous buffer solution such as a phosphate buffer solution, a boric acid buffer solution and a carbonic acid buffer solution can be suitably used.

As the above-described carbodiimide, 1-ethyl-3-(3-dimethylaminopropyl)carbodiimide or the like can be used. Moreover, N-hydroxysuccinimide, sulfo-N-hydroxysuccinimide or the like may be allowed to coexist with the carbodiimide, in doing so, a further stable active ester group may be derived from an active ester group induced by the carbodiimide.

In the amide bonding reaction of the biomolecule with the functional molecule-containing silica nanoparticles on which the linker molecule is bonded, the reaction is preferably performed by allowing from 10 to 500 μg of the biomolecule having the amino group to coexist with 1 mg of the functional molecule-containing silica nanoparticles on which the linker molecule is bonded.

The reaction temperature is preferably from 0 to 60° C., more preferably from 10 to 40° C. The reaction time is preferably 5 minutes or more, more preferably from 5 to 600 minutes.

When the reaction is performed through the above-mentioned steps, the functional molecule-containing silica nanoparticles on which the biomolecule is bonded is obtained in the aqueous solvent.

In order to extinguish reactivity of the active ester remaining in the functional molecule-containing silica nanoparticles on which the biomolecule is bonded as obtained above, bovine serum albumin, casein or the like may be further added thereto and mixed.

In the functional molecule-containing silica nanoparticles on which the biomolecule is bonded as prepared by the production method of the present invention, the bonding amount of the biomolecule can be measured by an ordinary method. For example, when the biomolecule is proteins, the bonding amount is determined in measuring by a common protein analysis method (e.g., UV method, Lowry method, or Bradford method). When the biomolecule is nucleic acid, the amount can be quantitatively determined by measuring absorbence (at 260 nm) of a liquid in which the nucleic acid is dissolved.

The mean particle diameter of the functional molecule-containing silica nanoparticles on which the biomolecule is bonded prepared by the production method of the present invention is preferably from 1 to 1,000 nm, more preferably from 20 to 500 nm.

In the present invention, the mean particle diameter means an average value of equivalent circle diameter (average equivalent-circle diameter). The equivalent circle corresponds to the value obtained by measuring the occupied area of the particles using an image processing equipment based on the project area of the total 50 pieces of randomly-selected particles selected from an image obtained under transmission electron microscope (TEM) or scanning electron microscope (SEM) or the like, and dividing the total occupied area with the number of the selected particles (50 pieces).

The mean particle diameter does not reflect diameter of secondary particle formed by aggregation of primary particles.

In the functional molecule-containing silica nanoparticles on which a biomolecule is bonded prepared by the production method of the present invention, the variation coefficient, what is called CV value, of the particle size distribution is not particularly limited, and preferably 10% or less, and more preferably 8% or less.

In the functional molecule-containing silica nanoparticles on which the biomolecule is bonded as prepared by the production method of the present invention, the bonding amount of the biomolecule shows a positive correlation with the amount of the thiol group introduced onto the functional molecule-containing silica nanoparticles, and therefore the bonding amount of the biomolecule can be precisely controlled by controlling the introducing amount of the thiol group. For example, the amount of the thiol group on the surface of the particles is constant among the functional molecule-containing silica nanoparticles having the thiol group prepared under specific identical conditions, and therefore the functional molecule-containing silica nanoparticles having a predetermined amount of biomolecule can be consistently obtained. Thus, upon using the functional molecule-containing silica nanoparticles on which the biomolecule is bonded for an intended detection test or analytical test, a fluctuation of an obtained output value (for example, fluorescence intensity) can be significantly suppressed, and thus a test that is excellent in quantitative properties and reliability can be conducted. Moreover, when the amount of the thiol group on the surface of the functional molecule-containing silica nanoparticles is measured, the bonding amount of the biomolecule can be estimated. Accordingly, if a plurality of samples of functional molecule-containing silica nanoparticles each of which has different bonding amount of the thiol group are prepared, the functional molecule-containing silica nanoparticles on which an intended amount of the biomolecule is bonded can be prepared according to a purpose.

In the production method of the present invention, the functional molecule-containing silica nanoparticles having the thiol group on the surface thereof is used. Only when the functional molecule-containing silica nanoparticles having the thiol group are used, the biomolecule and the functional molecule-containing silica nanoparticles can be very easily and uniformly bonded by a covalent bonding reaction using the maleimido group and the active ester group. As a method for strongly and stably bonding the functional molecule-containing silica nanoparticles with the biomolecule through a linker, for example, a method can also be considered in which an amino group is introduced onto the surface of the functional molecule-containing silica nanoparticles, in place of the thiol group, to allow covalent bonding between an active ester group of the linker molecule and the amino group, and further to allow covalent bonding between an maleimido group of the linker molecule and a thiol group of the biomolecule. However, practically, the functional molecule-containing silica nanoparticles, the surface of which the amino group is introduced onto, significantly aggregate, and have poor usefulness. The reason may be that the silica nanoparticles having the amino group on the surface thereof has further increased hydrophobicity as compared to the silica nanoparticles having the thiol group on the surface thereof.

In the production method of the present invention, as the linker molecule, one having various carbon chain length or one including an aromatic ring can be selected. When a structure of the linker molecule is appropriately selected, activity of the biomolecule bonded with the surface of the functional molecule-containing silica nanoparticles can be maximized. The reason why the activity of the biomolecule is different depending on the structure of the linker molecule is yet uncertain, an optimum structure of the linker molecule is considered to change depending on a degree of separation of a part to be bonded with the linker molecule from a part exhibiting the activity in the biomolecule, or depending on a degree of hydrophilic-hydrophobic properties of the biomolecule.

The biomolecule-bonding functional silica nanoparticles of the present invention can be obtained by the above-mentioned production method of the present invention. Specifically, the particles have a structure in which the thiol group of the silica nanoparticles containing the functional molecule and the maleimido group of the linker molecule are bonded by the thioether bond, and a structure in which the carboxyl group of the linker molecule, and the amino group of the biomolecule are bonded by the amide bond.

The functional molecule-containing silica nanoparticles having the thiol group, the linker molecule and the biomolecule are synonymous with ones as explained in the above-mentioned production method of the present invention.

The biomolecule-bonding functional silica nanoparticles of the present invention can be used as a labeling reagent, and can also be incorporated into various kinds of analytical reagents as the labeling reagent.

The labeling reagent including the biomolecule-bonding functional silica nanoparticles of the present invention is excellent in preservation stability and hard to cause performance deterioration, and the analytical result using the analytical reagent containing this reagent has, as presented in Examples described later, very high reproducibility and excellent reliability.

The colloid according to the present invention is formed by dispersing the biomolecule-bonding functional silica nanoparticles into the dispersion medium.

The above-described dispersion medium is not particularly limited, and may be one that uniformly disperses the functional molecule-containing silica nanoparticles on which the biomolecule is bonded according to the present invention, but is preferably a hydrophilic solvent. Specific examples for the hydrophilic solvents include water, methanol, ethanol, a mixed solvent of water and methanol, a mixed solvent of water and ethanol, and a buffer solution such as PBS (phosphate buffered saline), a Tris buffer solution and an HEPES buffer solution.

Further, from a viewpoint of further preventing the non-specific adsorption of the functional molecule-containing silica nanoparticles on which the biomolecule is bonded, an arbitrary blocking agent such as polyethylene glycol (PEG) and bovine serum albumin (BSA) may be incorporated into composite particle colloid according to the present invention. Moreover, a preservative such as sodium azide may be incorporated thereinto.

In the colloid according to the present invention, the functional molecule-containing silica nanoparticles on which the biomolecule is bonded according to the present invention stably exist, and the colloid can be stored for a long period of time without significantly adversely affecting the activity of the biomolecule.

The colloid of the present invention may be used as a labeling reagent solution. Further, the colloid can be used for the preparation of labeled reagent contained in the analytical reagent.

The analytical reagent according to the present invention contains the biomolecule-bonding functional silica nanoparticles of the present invention, and is used as a detection reagent for detecting a target molecule that can be recognized by the biomolecule, a quantitative reagent for quantitatively determining the target molecule, a separation reagent for separating the target molecule, a collection reagent for isolating and collecting the target molecule, a labeling reagent for labeling the target molecule, or the like.

Specific examples of a combination of the above-described biomolecule and the target molecule include a combination of a nucleic acid and a nucleic acid having complementary sequence thereto, a combination of an antibody and an antigen, a combination of an antigen and an antibody, a combination of an enzyme and a substrate, a combination of a receptor and a ligand, and a combination of a ligand and a receptor.

Specific examples of the analytical reagents according to the present invention include, for example, an immunochromatography device having a test strip in which the biomolecule-bonding functional silica nanoparticles of the present invention are retained to a conjugate pad.

EXAMPLES

The present invention is described in more detail based on examples shown below, but the invention is not limited to them.

Reference Example 1

Preparation of Functional Molecule-Containing Silica Nanoparticles Having Thiol Group—1

(Preparation of Functional Molecule-Containing Silica Nanoparticles)

Silica nanoparticles containing Carboxy Rhodamine-6G being a fluorescent molecule as a functional molecule were prepared.

Was 3.1 mg of 5- (and -6)-carboxy rhodamine 6G·succinimidyl ester (trade name, manufactured by EMP Biotech GmbH) dissolved in 1 mL dimethyl formamide (DMF). Then, 1.2 µL of APS (manufactured by Shin-Etsu Silicone Co., Ltd.) was added thereto and the reaction was carried out for 1 hour at room temperature (23° C.). Then, 5- (and -6)-carboxy rhodamine 6G-APS composite (5 mM) was obtained.

Was 600 µL of the obtained solution of 5- (and -6)-carboxy rhodamine 6G-APS composite admixed with 140 mL of ethanol, 6.5 mL of TEOS (manufactured by Shin-Etsu Silicone Co., Ltd.), 20 mL of distilled water, and 15 mL of 28 mass % aqueous ammonia, and the reaction was progressed at room temperature for 24 hours.

The reaction solution was centrifuged at a gravitational acceleration of 18,000×g for 30 minutes, and the supernatant was removed. Was 4 mL of distilled water added to the precipitated functional molecule-containing silica nanoparticles, dispersed the particles, and the dispersion was centrifuged again at a gravitational acceleration of 18,000×g for 30 minutes. Further, the washing operation was repeated twice additionally for removal of the unreacted TEOS, ammonia and others contained in the dispersion of silica nanoparticles containing the fluorescent molecule, and thus obtained 1.65 g of silica nanoparticles containing the fluorescent molecule having the mean particle diameter of 271 nm. Yield ratio ca. 94%.

(Introduction of Thiol Group)

Then, 20 mg of particles obtained as described above was dispersed into 1 mL of mixed solution of water/ethanol=¼. There, 20 μL of MPS (manufactured by Wako Pure Chemical Industries, Ltd.) was added. Subsequently, 50 μL of 28% aqueous ammonia was added thereto, and the resultant mixture was mixed at room temperature for 4 hours.

The reaction solution was centrifuged at a gravitational acceleration of 18,000×g for 30 minutes, and the supernatant was removed. To silica nanoparticles precipitated, 1 mL of distilled water was added to disperse the particles, and the resultant mixture was again centrifuged at a gravitational acceleration of 18,000×g for 30 minutes. The present washing operation was further repeated twice to remove unreacted MPS, ammonia and so forth that were contained in a dispersion liquid of fluorescent molecule-containing silica nanoparticles having a thiol group, and thus fluorescent molecule-containing silica nanoparticles on which the thiol group is introduced (hereinafter, referred to as thiol group-introduced fluorescent silica nanoparticles A) were obtained.

(Elemental Analysis of Sulfur Element)

An elemental analysis was performed using 20 mg of above-described thiol group-introduced fluorescent silica nanoparticles A. As a result, the content of a sulfur element in the thiol group-introduced fluorescent silica nanoparticles A was 374 ppm with respect to the total weight of the particles.

Reference Example 2

Preparation of Functional Molecule-Containing Silica Nanoparticles Having Thiol Group—2

Aqueous ammonia of 14 mass % was diluted by 5 times with ethanol, and thus 3.5 mL of aqueous ammonia-containing solvent was prepared. To the aqueous ammonia-containing solvent, 30 μL (135 μmol) of TEOS (manufactured by Shin-Etsu Silicone Co., Ltd.) and 30 μL of 5-(and 6-)Carboxy Rhodamine-6G-APS composite (5 mM) prepared in Reference Example 1 were added, and the resultant mixture was stirred at 40° C. for 30 minutes, and thus a solution in which core particles containing fluorescent molecules was formed (hereinafter, occasionally referred to as a core fluorescent particle-containing solution) was obtained.

To the above-described core fluorescent particle-containing solution, 30 μL (135 μmol) of TEOS (manufactured by Shin-Etsu Silicone Co., Ltd.), and 11 μL (110 nmol) of 5-(and 6-)Carboxy Rhodamine-6G-APS dissolved into dimethylformamide (DMF, manufactured by Wako Pure Chemical Industries, Ltd.) to be a concentration of 10 mM were further added, the resultant mixture was stirred at 40° C. for 30 minutes to form a shell layer on core fluorescent particles, and thus a solution containing fluorescent molecule-containing silica nanoparticles (hereinafter. occasionally referred to as first fluorescent silica nanoparticles) was obtained.

To the above-described first fluorescent silica nanoparticles-containing solution, 10 μL (45 μmol) of TEOS, and 5.3 μL (53 nmol) of 5-(and 6-)Carboxy Rhodamine-6G-APS dissolved into DMF to be a concentration of 10 mM were further added, the resultant mixture was stirred at 40° C. for 30 minutes to further form a shell layer on first fluorescent silica nanoparticles, and thus a solution containing particles (hereinafter. occasionally referred to as second fluorescent silica nanoparticles) was obtained.

In order to introduce a mercaptopropyl group onto a surface of second fluorescent silica nanoparticles, 20 μL of mixed solution of MPS (manufactured by Wako Pure Chemical Industries, Ltd.) and TEOS as prepared at a mixing ratio of conditions 1 in Table 1 (MPS/TEOS mixed solution) was further added to the above-described second silica nanoparticles-containing solution. The resultant mixture was stirred at room temperature for 30 minutes, a solution containing fluorescent molecule-containing silica nanoparticles having a hydroxyl group and a mercaptopropyl group on the surface layer thereof (hereinafter, referred to as thiol group-introduced fluorescent silica nanoparticles B) was obtained. In the same manner, solutions containing fluorescent molecule-containing silica nanoparticles prepared by adding MPS/TEOS mixed solutions prepared at the mixing ratios of conditions 2 and 3 in Table 1 (hereinafter referred to as thiol group-introduced fluorescent silica nanoparticles C and thiol group-introduced fluorescent silica nanoparticles D, respectively) were also prepared.

In Table 1, "Addition amount of MPS with respect to total addition amount of TEOS and MPS (TEOS+MPS)" represents the total addition amount of MPS with respect to the total amount of TEOS and MPS added to an aqueous ammonia-containing solvent through the above-described total steps. Further, the MPS/TEOS mixed solution was prepared just before addition.

TABLE 1

| | MPS concentration in mixed solution (20 μL) of MPS and TEOS | TEOS concentration in mixed solution (20 μL) of MPS and TEOS | Addition amount of MPS with respect to total addition amount of TEOS and MPS (TEOS + MPS) |
|---|---|---|---|
| Condition 1 | 25 vol % (27 μmol) | 75 vol % (68 μmol) | 5.5 vol % (TEOS + MPS (mol):MPS (mol) = 1:0.28) |
| Condition 2 | 50 vol % (54 μmol) | 50 vol % (45 μmol) | 11.1 vol % (TEOS + MPS (mol):MPS (mol) = 1:0.55) |
| Condition 3 | 75 vol % (81 μmol) | 25 vol % (23 μmol) | 16.6 vol % (TEOS + MPS (mol):MPS (mol) = 1:0.78) |

(Elemental Analysis of Sulfur Element)

An elemental analysis was performed by using 20 mg of thiol group-introduced fluorescent silica nanoparticles B to D as obtained under conditions 1 to 3, respectively. As a result, the content of a sulfur element was 319 ppm for thiol group-introduced fluorescent silica nanoparticles B, 682 ppm for thiol group-introduced fluorescent silica nanoparticles C, and 1,401 ppm for thiol group-introduced fluorescent silica nanoparticles D, with respect to the total weight of particles, respectively.

Example 1

Preparation of Functional Molecule-Containing Silica Nanoparticles on which Biomolecule is Bonded—1

To 40 μL of dispersion liquid (concentration 25 mg/mL, a dispersion medium: distilled water) of thiol group-introduced fluorescent silica nanoparticles A (mean particle diameter 260 nm) prepared in Reference Example 1, 460 µL of DMF was added, and the resultant mixture was centrifuged at a gravitational acceleration of 15,000×g for 10 minutes. A supernatant was removed, 500 µL of DMF was added thereto, the resultant mixture was centrifuged and a supernatant was removed. Then, 500 µL of DMF was again added to disperse thiol group-introduced fluorescent silica nanoparticles A. In there, 1 mg of 3-maleimidobenzoic acid as a linker molecule was added, the resultant mixture was mixed for 30 minutes, and thus a thioether bond was formed between the maleimido group of the above-described linker molecule and the thiol group of thiol group-introduced fluorescent silica nanoparticles A.

This reaction mixture was centrifuged at gravitational acceleration of 15,000×g for 10 minutes, a supernatant was removed, and then 84.0 µL of distilled water was added to disperse particles. Subsequently, 100 µL of 0.5 M MES (2-morpholinoethane sulfonic acid) (pH 6.0), 230.4 µL of 50 mg/mL NHS (N-hydroxysuccinimide), 75 µL of 19.2 mg/mL EDC (1-ethyl-3-(3-dimethylaminopropyl)carbodiimide) were added thereto, and the resultant mixture was mixed. There, 10.6 µL of anti-influenza A nucleoprotein antibody (6.2 mg/mL, manufactured by HyTest, Ltd.) was added, and the resultant mixture was mixed for 10 minutes.

The reaction solution was centrifuged at a gravitational acceleration of 15,000×g for 10 minutes, and the supernatant was removed. There, 400 µL of 10 mM $KH_2PO_4$ (pH 7.5) was added to disperse particles. Subsequently, the reaction solution was centrifuged at a gravitational acceleration of 15,000×g for 10 minutes, and the supernatant was removed. Then, 400 µL of 10 mM $KH_2PO_4$ (pH 7.5) was again added to disperse particles, and thus colloid was obtained.

Protein quantitative determination was performed by using this colloid as a sample. For protein quantitative determination, Pierce BCA Protein Assay Kit (manufactured by Thermo Fisher Scientific K.K.) was used. As a result, the bonding amount of the antibody was 42 mg per 1 g of fluorescent molecule-containing silica nanoparticles on which the antibody was bonded.

Subsequently, 10 µL of 10% BSA was added to the above-described colloid, and the resultant mixture was mixed for 10 minutes. The reaction solution was centrifuged at a gravitational acceleration of 15,000×g for 10 minutes, and the supernatant was removed. Then, 500 µL of 10 mM $KH_2PO_4$ (pH 7.5) was added to disperse particles, the resultant mixture was centrifuged at a gravitational acceleration of 15,000×g for 10 minutes, and a supernatant was removed. Then, 400 µL of 10 mM $KH_2PO_4$ (pH 7.5) was again added to disperse particles, and thus colloid in which functional molecule-containing silica nanoparticles on which the anti-influenza A nucleoprotein antibody was bonded (hereinafter, referred to as colloid A of the present invention) were dispersed was obtained.

Example 2

Preparation of Functional Molecule-Containing Silica Nanoparticles on which Biomolecule is Bonded—2

Bonding process of the antibody was performed by using thiol group-introduced silica nanoparticles B to D prepared in Reference Example 2 in the same manner as the method in Example 1, and thus each colloid into which particles were dispersed was obtained. As a result of protein quantitative determination, the bonding amount of the antibody per 1 g of fluorescent molecule-containing silica nanoparticles on which the antibody was bonded was 32 mg when thiol group-introduced silica nanoparticles B were used, 48 mg when thiol group-introduced silica nanoparticles C were used, and 55 mg when thiol group-introduced silica nanoparticles D were used.

Subsequently, 10 µL of 10% BSA was added to the above-described each colloid, and each resultant mixture was mixed for 10 minutes. The reaction solution was centrifuged at a gravitational acceleration of 15,000×g for 10 minutes, and the supernatant was removed. Then, 500 µL of 10 mM $KH_2PO_4$ (pH 7.5) was added to disperse particles, the resultant mixture was centrifuged at a gravitational acceleration of 15,000×g for 10 minutes, and a supernatant was removed. Then, 400 µL of 10 mM $KH_2PO_4$ (pH 7.5) was again added to disperse particles, and thus colloid in which functional molecule-containing silica nanoparticles on which the anti-influenza A nucleoprotein antibody was bonded (hereinafter, referred to as colloid B to D according to the present invention, corresponding to the above-described thiol group-introduced silica nanoparticles B to D, respectively) were dispersed was obtained.

Comparative Example 1

Preparation of Functional Molecule-Containing Silica Nanoparticles on which Biomolecule is Adsorbed—1

To 40 µL of dispersion liquid (concentration 25 mg/mL, a dispersion medium: distilled water) of fluorescent molecule-containing silica nanoparticles (mean particle diameter 260 nm) before introduction of a thiol group as described in Reference Example 1, 449.4 µL of 10 mM $KH_2PO_4$ (pH 7.5) and 10.6 µL of the anti-influenza A nucleoprotein antibody (6.2 mg/mL, manufactured by HyTest, Ltd.) were added, and the resultant mixture was mixed for 10 minutes.

The reaction solution was centrifuged at a gravitational acceleration of 15,000×g for 10 minutes, and the supernatant was removed. There, 400 µL of 10 mM $KH_2PO_4$ (pH 7.5) was added to disperse particles. The reaction solution was centrifuged at a gravitational acceleration of 15,000×g for 10 minutes, and the supernatant was removed. Then, 400 µL of 10 mM $KH_2PO_4$ (pH 7.5) was again added to disperse particles.

Protein quantitative determination was performed by using this colloid as a sample. For protein quantitative determination, Pierce BCA Protein Assay Kit (manufactured by Thermo Fisher Scientific K.K.) was used. As a result, the bonding amount of the antibody was 35 mg per 1 g of fluorescent molecule-containing silica nanoparticles on which the antibody was adsorbed.

Subsequently, 10 µL of 10% BSA was added, and the resultant mixture was mixed for 10 minutes. The reaction solution was centrifuged at a gravitational acceleration of 15,000×g for 10 minutes, and the supernatant was removed. Then, 500 µL of 10 mM $KH_2PO_4$ (pH 7.5) was added to disperse particles, the resultant mixture was centrifuged at a gravitational acceleration of 15,000×g for 10 minutes, and a supernatant was removed. Then, 400 µL of 10 mM $KH_2PO_4$ (pH 7.5) was again added to disperse particles, and thus 400 µL of 2.5 mg/mL colloid in which functional molecule-containing silica nanoparticles on which the anti-influenza A nucleoprotein antibody was adsorbed (hereinafter, referred to as comparative colloid E) were dispersed was obtained.

Test Example 1

Preservation Stability Test

Figure 2:
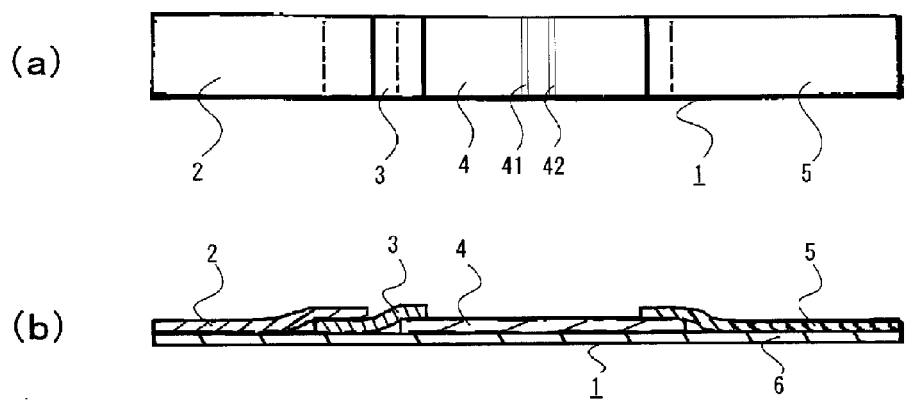
FIG. 2 is a drawing schematically showing structure of a test strip used in Example.

An immunochromatography-purpose test strip including a conjugate pad prepared by applying any of colloid A to D according to the present invention prepared in Examples 1 and 2 and comparative colloid E prepared in Comparative Example, followed by drying was prepared. Preparation of the test strip was performed by an ordinary method. The structure of the prepared test strip is shown in FIG. 2.

A test was conducted using PBS (phosphate buffered saline) as a test liquid immediately after preparation of the test strip, after 7 days therefrom and after 14 days therefrom. The test was conducted by adding 100 µL of PBS dropwise to a conjugate pad, and executed for every 5 strips for each test. After 30 minutes from dropwise addition of the test liquid, the pad was irradiated with a laser beam using a laser diode as an excitation light source, and using a scanner for receiving fluorescence with a photodiode, a fluorescence intensity distribution of a membrane was measured while moving the above-described scanner from a conjugate pad side to an absorbent pad side. An intensity of a control line was evaluated from the thus obtained fluorescence profile of the membrane, and a change of fluorescence intensity of the control line with time elapsed after preparation of the test strip was evaluated. An antibody having bonding affinity with the anti-influenza A nucleoprotein antibody (anti-mouse IgG antibody, manufactured by BIODESIGN International Inc.) was immobilized to the control line.

The results are shown in Table 2 below. In Table 2, a reduction ratio (%) of line intensity was calculated with regard to the fluorescence intensity of the test line upon testing a test strip immediately after preparation of the test strip as 100%. For example, a reduction ratio of 10% means 90% of fluorescence intensity with respect to the fluorescence intensity upon testing immediately after preparation of the test strip as 100%. In Table 2, the reduction ratio of line intensity presents a mean value of 5-fold measurements. Moreover, a fluctuation in fluorescence intensity among 5-fold measurements (coefficient of variation) was also presented in Table 2.

TABLE 2

|  | Reduction ratio of line intensity (%) | | Fluctuation of line intensity (Coefficient of variation among 5-fold measurements (CV)) | |
| --- | --- | --- | --- | --- |
|  | After 7 days | After 14 days | After 7 days | After 14 days |
| Colloid A | 2.1 | 3.6 | 2.7 | 3.5 |
| Colloid B | 3.8 | 5.0 | 1.8 | 3.1 |
| Colloid C | 2.2 | 3.4 | 2.0 | 2.9 |
| Colloid D | 1.5 | 2.1 | 2.6 | 3.1 |
| Colloid E | 14.2 | 27.1 | 9.6 | 11.9 |

As presented in Table 2, in the test strip using the conjugate pad on which comparative colloid E was applied, the line intensity decreased by as high as 14.2% on $7^{th}$ day, and 27.1% on $14^{th}$ day as compared to the line intensity immediately after preparation.

On the other hand, in the test strips using the conjugate pads to which any of colloid A to D according to the present invention were applied, a reduction ratio of line intensity was suppressed to only 5% or less even after elapse of 14 days as compared to the line intensity immediately after preparation. These result reflects a fact that the biomolecule strongly bonds with the surface of the functional molecule-containing silica nanoparticles in the functional molecule-containing silica nanoparticles on which the biomolecule is bonded prepared by the production method of the present invention, and as a result, the biomolecule is further hard to peel from the surface of particles in the drying step during preparation of the conjugate pad, and the biomolecule is further hard to peel from the surface of particles in a process in which particles are eluted from the conjugate pad by adding dropwise the test liquid to the conjugate pad upon testing. Moreover, this result also reflects a fact that the biomolecule is further hard to peel from the surface of the functional molecule-containing silica nanoparticles even when the particles are brought in contact with the conjugate pad in a dry state, or with a membrane during analysis.

The result of Table 2 shows that a fluctuation in line intensity among measurements was large, and a coefficient of variations (CV) of line intensity in 5-fold measurements was 9.6 to 11.9 in the test strip using the conjugate pad on which comparative colloid E was applied. On the other hand, CV of line intensity in 5-fold measurements was significantly as small as 1.8 to 3.5 and significantly excellent reproducibility was obtained in the test strip using the conjugate pad on which any of colloid A to D according to the present invention were applied. Such significant rise in reproducibility only by changing a structure of the labeling reagent that is only one constituent in immunochromatography reagent exceeds expectation of those skilled in the art.

Example 3

Preparation of Functional Molecule-Containing Silica Nanoparticles on which Biomolecule is Bonded—3

Thiol group-introduced fluorescent silica nanoparticles A prepared in Reference Example 1 were used as functional molecule-containing silica particles and an antibody processed to Fab (Fab Anti-MOUSE IgG (H&L) (GOAT) Antibody (manufactured by Rockland Inc.)) was used as an antibody, and the silica particles and the antibody were bonded in the same manner as the method in Example 1.

Protein quantitative determination was performed by using the obtained colloid as a sample. As a result, the bonding amount of the antibody was 36 mg per 1 g of fluorescent molecule-containing silica nanoparticles on which the antibody was bonded.

Subsequently, remaining colloid was stored for one month at 4° C., and then centrifuged at a gravitational acceleration of 15,000×g for 10 minutes, and a supernatant was removed. Then, 500 µL of 10 mM $KH_2PO_4$ (pH 7.5) was added to disperse particles, the resultant mixture was centrifuged at a gravitational acceleration of 15,000×g for 10 minutes, and a supernatant was removed. As a result of performing protein quantitative determination using, as a sample, colloid prepared by adding 10 mM $KH_2PO_4$ (pH 7.5) again in order to disperse particles, the bonding amount of the antibody was 34 mg per 1 g of fluorescent molecule-containing silica nanoparticles on which the antibody is bonded.

Thus, when the method of the present invention is applied, a sufficient amount of even the antibody processed to Fab could be bonded with the fluorescent molecule-containing silica nanoparticles. Further, this bond was also found to be very stably maintained even after storage for a long period of time.

Comparative Example 2

Preparation of Functional Molecule-Containing Silica Nanoparticles on which Biomolecule is Adsorbed—2

Thiol group-introduced fluorescent silica nanoparticles A prepared in Reference Example 1 were used as functional molecule-containing silica particles and an antibody processed to Fab (Fab Anti-MOUSE IgG (H&L) (GOAT) Antibody (manufactured by Rockland Inc.)) was used as an antibody, and the antibody were adsorbed in the same manner as the method in Comparative example 1.

Protein quantitative determination was performed by using the obtained colloid as a sample. As a result, the bonding amount of the antibody was 6 mg per 1 g of fluorescent molecule-containing silica nanoparticles on which the antibody was adsorbed.

Subsequently, remaining colloid was stored for one month at 4° C., and then centrifuged at a gravitational acceleration of 15,000×g for 10 minutes, and a supernatant was removed. Then, 500 μL of 10 mM $KH_2PO_4$ (pH 7.5) was added to disperse particles, the resultant mixture was centrifuged at a gravitational acceleration of 15,000×g for 10 minutes, and a supernatant was removed. As a result of performing protein quantitative determination using, as a sample, colloid prepared by adding 10 mM $KH_2PO_4$ (pH 7.5) again in order to disperse particles, the bonding amount of the antibody was 1 mg or less per 1 g of fluorescent molecule-containing silica nanoparticles on which the antibody is adsorbed.

Thus, a sufficient amount of the antibody processed to Fab could not be adsorbed with the fluorescent molecule-containing silica nanoparticles, when the Fab was attempted to adsorb to the fluorescent molecule-containing silica nanoparticles. Further, the antibody processed to Fab was found to be easily separated from the fluorescent molecule-containing silica nanoparticles, and thus, the colloid was difficult to store for a long period of time.

Having described our invention as related to the present embodiments, it is our intention that the invention not be limited by any of the details of the description, unless otherwise specified, but rather be construed broadly within its spirit and scope as set out in the accompanying claims.

This application claims priority on Patent Application No. 2011-97880 filed in Japan on Apr. 26, 2011, which is entirely herein incorporated by reference.

REFERENCE SIGNS LIST

1 Test strip
2 Sample pad
3 Conjugate pad
4 Antibody-immobilized membrane
41 Judgment region (Test line)
42 Control line
5 Absorbent pad
6 Backing sheet

The invention claimed is:

1. A method of producing functional molecule-containing silica nanoparticles on which a biomolecule is bonded, comprising the steps of:
    mixing organoalkoxysilane having a functional molecule and tetraalkoxysilane in an ammonia-containing aqueous solvent to allow formation of silica core particles containing the functional molecule in the solvent, thereby obtaining a dispersion liquid of the core particles; and
    adding organoalkoxysilane having a thiol group and tetraethoxysilane (TEOS) to the dispersion liquid obtained in the above step, thereby allowing formation of a shell layer on the silica core particles to obtain silica nanoparticles containing the functional molecule and having the thiol group on the surface thereof, wherein the amount of sulfur element in the silica nanoparticles containing the functional molecule and having the thiol group on the surface thereof is from 200 ppm to 2,000 ppm with respect to the weight of the silica nanoparticles;
    allowing the silica nanoparticles containing the functional molecule and having the thiol group on the surface thereof to coexist with a linker molecule having a maleimido group and a carboxyl group in an aprotic solvent, thereby allowing formation of a thioether bond between the thiol group and the maleimido group, and obtaining functional molecule-containing silica nanoparticles on which the linker molecule is bonded; and
    allowing the functional molecule-containing silica nanoparticles on which the linker molecule is bonded to coexist with a carbodiimide and a biomolecule having an amino group in an aqueous solvent, thereby allowing formation of an amide bond between the carboxyl group active esterified by the carbodiimide, and the amino group of the biomolecule,
    wherein the bonding amount of the biomolecule is controlled by the amount of the thiol group, and
    wherein a mean particle diameter of the functional molecule-containing silica nanoparticles on which the biomolecule is bonded is from 20 to 500 nm.

2. The production method according to claim 1, wherein the biomolecule is selected from the group consisting of a protein, a polyamino acid, a peptide, a nucleic acid, a peptide nucleic acid, a sugar, a sugar chain, a ligand, a receptor and an aptamer.

3. A method of producing functional molecule-containing silica nanoparticles on which a biomolecule is bonded, comprising the steps of:
    mixing organoalkoxysilane having a functional molecule and tetraalkoxysilane in an ammonia-containing aqueous solvent to allow formation of silica core particles containing the functional molecule in the solvent, thereby obtaining a dispersion liquid of the core particles; and
    adding organoalkoxysilane having a thiol group and tetraethoxysilane (TEOS) to the dispersion liquid obtained in the above step, thereby allowing formation of a shell layer on the silica core particles to obtain silica nanoparticles containing the functional molecule and having the thiol group on the surface thereof, wherein the amount of sulfur element in the silica nanoparticles containing the functional molecule and having the thiol group on the surface thereof is from 200 ppm to 2,000 ppm with respect to the weight of the silica nanoparticles;
    allowing the silica nanoparticles containing the functional molecule and having the thiol group on the surface thereof to coexist with a linker molecule having a maleimido group and a carboxyl group in an aprotic solvent, thereby allowing formation of a thioether bond between the thiol group and the maleimido group, and obtaining functional molecule-containing silica nanoparticles on which the linker molecule is bonded;
    allowing the functional molecule-containing silica nanoparticles on which the linker molecule is bonded to coexist with a carbodiimide in an aqueous solvent, thereby allowing active esterification of the carboxyl group; and
    allowing coexistence of a biomolecule having an amino group in the aqueous solvent, thereby forming an amide bond between the active ester group and the amino group of the biomolecule,
    wherein the bonding amount of the biomolecule is controlled by the amount of the thiol group, and wherein a mean particle diameter of the functional molecule-containing silica nanoparticles on which the biomolecule is bonded is from 20 to 500 nm.

4. The production method according to claim 3, wherein the linker molecule is selected from the group consisting of maleimidoacetic acid, 4-maleimidobutyric acid, 5-maleimidovaleric acid, maleimidocaproic acid and 3-maleimidobenzoic acid.

5. The production method according to claim 3, wherein the aprotic solvent is dimethylformamide or dimethylsulfoxide.

6. The production method according to claim 3, wherein the biomolecule is selected from the group consisting of a protein, a polyamino acid, a peptide, a nucleic acid, a peptide nucleic acid, a sugar, a sugar chain, a ligand, a receptor and an aptamer.

7. The production method according to claim 3, wherein the biomolecule is an antibody selected from the group consisting of an immunoglobulin, F(ab')$_2$, Fab, a chemically synthesized polyamino acid, a recombinant protein and a recombinant polyamino acid.

8. The production method according to claim 3, wherein the functional molecule is selected from the group consisting of a fluorescent molecule, a light-absorbing molecule, a magnetic molecule, a radioactive molecule and a pH-sensitive molecule.

9. A method of producing functional molecule-containing silica nanoparticles on which a biomolecule is bonded, comprising the steps of:
   mixing organoalkoxysilane having a functional molecule and tetraalkoxysilane in an ammonia-containing aqueous solvent to allow formation of silica core particles containing the functional molecule in the solvent, thereby obtaining a dispersion liquid of the core particles; and
   adding organoalkoxysilane having a thiol group and tetraethoxysilane (TEOS) to the dispersion liquid obtained in the above step, thereby allowing formation of a shell layer on the silica core particles to obtain silica nanoparticles containing the functional molecule and having the thiol group on the surface thereof, wherein the amount of sulfur element in the silica nanoparticles containing the functional molecule and having the thiol group on the surface thereof is from 200 m to 2 000 ppm with respect to the weight of the silica nanoparticles;
   allowing the silica nanoparticles containing the functional molecule and having the thiol group on the surface thereof to coexist with a linker molecule having a maleimido group and an active ester group in an aprotic solvent, thereby allowing formation of a thioether bond between the thiol group and the maleimido group, and obtaining functional molecule-containing silica nanoparticles on which the linker molecule is bonded; and
   allowing the functional molecule-containing silica nanoparticles on which the linker molecule is bonded to coexist with a biomolecule having an amino group in an aqueous solvent, thereby allowing formation of an amide bond between the active ester group and the amino group of the biomolecule,
   wherein the bonding amount of the biomolecule is controlled by the amount of the thiol group, and
   wherein a mean particle diameter of the functional molecule-containing silica nanoparticles on which the biomolecule is bonded is from 20 to 500 nm.

10. The production method according to claim 9, wherein the biomolecule is selected from the group consisting of a protein, a polyamino acid, a peptide, a nucleic acid, a peptide nucleic acid, a sugar, a sugar chain, a ligand, a receptor and an aptamer.

* * * * *